United States Patent
Sinha et al.

(10) Patent No.: US 10,605,640 B2
(45) Date of Patent: Mar. 31, 2020

(54) APPARATUS AND METHOD FOR VISUALIZATION OF PARTICLES SUSPENDED IN A FLUID AND FLUID FLOW PATTERNS USING ULTRASOUND

(75) Inventors: Dipen N. Sinha, Los Alamos, NM (US); Curtis F. Osterhoudt, Los Alamos, NM (US); Cristian Pantea, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 403 days.

(21) Appl. No.: 13/225,787

(22) Filed: Sep. 6, 2011

(65) Prior Publication Data
US 2012/0227473 A1  Sep. 13, 2012

Related U.S. Application Data

(60) Provisional application No. 61/379,888, filed on Sep. 3, 2010.

(51) Int. Cl.
*G01F 1/74*  (2006.01)
*G01F 1/66*  (2006.01)
(Continued)

(52) U.S. Cl.
CPC ............ *G01F 1/74* (2013.01); *G01F 1/66* (2013.01); *G01F 1/662* (2013.01); *G01F 1/7082* (2013.01);
(Continued)

(58) Field of Classification Search
USPC .......................... 73/861.18, 861.19, 861.27, 73/861.25–861.31, 61.75, 61.79, 584–649;
(Continued)

(56) References Cited

U.S. PATENT DOCUMENTS 2,592,134 A * 4/1952 Firestone ........................ 73/629
3,705,261 A  12/1972 Langley
(Continued)

FOREIGN PATENT DOCUMENTS

WO  2012031292  3/2012

OTHER PUBLICATIONS

Needles, Andrew, et al. "Interframe clutter filtering for high frequency flow imaging." Ultrasound in medicine & biology 33.4 (2007): 591-600.*

*Primary Examiner* — Peter J Macchiarolo
*Assistant Examiner* — Alexander A Mercado
(74) *Attorney, Agent, or Firm* — Alston & Bird LLP

(57) ABSTRACT

An apparatus and method for real-time visualization of particulate matter suspended in a static or flowing fluid and fluid flow patterns in a pipe, tube, conduit, or other container, are described. Ultrasonic scanning and detection of scattered sound from the particles in the fluid create a real-time image of the particles, or of flow patterns in the liquid. A mechanical wobbler directs a piezoelectric transducer over a chosen angle in an oscillatory manner. The transducer is operated in a pulse-echo mode wherein the same transducer detects the return signal from the target region through which particles are passing and/or a flow is present. The pulse-echo measurements are made rapidly and continuously during a single sweep of the transducer over the chosen angle. Received signals are processed in the ultrasound scanner electronics module and displayed as an image in real-time.

30 Claims, 6 Drawing Sheets

(51) Int. Cl.
  *G01F 1/708* (2006.01)
  *G01N 29/26* (2006.01)
  *G01N 29/024* (2006.01)

(52) U.S. Cl.
  CPC ......... *G01N 29/024* (2013.01); *G01N 29/262* (2013.01)

(58) Field of Classification Search
  USPC ...................................................... 702/48, 54
  See application file for complete search history.

(56) References Cited

U.S. PATENT DOCUMENTS

| | | | |
|---|---|---|---|
| 4,034,744 A * | 7/1977 | Goldberg ..................... 600/445 |
| 4,120,291 A * | 10/1978 | Paton et al. .................... 73/620 |
| 4,279,167 A | 7/1981 | Erb et al. |
| 4,416,286 A * | 11/1983 | Iinuma et al. ................. 600/441 |
| 4,418,698 A * | 12/1983 | Dory ............................. 600/446 |
| 4,612,937 A * | 9/1986 | Miller ........................... 600/441 |
| 4,693,120 A | 9/1987 | Robinson |
| 4,694,434 A * | 9/1987 | von Ramm et al. ............... 367/7 |
| 4,852,575 A | 8/1989 | Nikoonahad |
| 4,882,934 A * | 11/1989 | Leffert et al. ............. 73/861.04 |
| 5,375,600 A * | 12/1994 | Melton et al. ................. 600/455 |
| 5,398,216 A * | 3/1995 | Hall et al. ...................... 367/90 |
| 5,521,883 A * | 5/1996 | Fage et al. ...................... 367/90 |
| 5,522,393 A * | 6/1996 | Phillips et al. ............... 600/455 |
| 5,540,230 A * | 7/1996 | Vilkomerson ............... 600/454 |
| 6,261,233 B1 * | 7/2001 | Kantorovich ................ 600/454 |
| 6,748,811 B1 | 6/2004 | Iwanaga et al. |
| 7,010,962 B2 | 3/2006 | Sinha |
| 7,601,121 B2 | 10/2009 | Pagoulatos et al. |
| 7,836,766 B2 * | 11/2010 | Jeong et al. .................... 73/603 |
| 2004/0144175 A1 * | 7/2004 | Sinha .............................. 73/579 |
| 2006/0020207 A1 * | 1/2006 | Pagoulatos et al. .......... 600/456 |
| 2007/0016046 A1 * | 1/2007 | Mozayeni et al. ............ 600/443 |
| 2008/0034844 A1 * | 2/2008 | Manneville ................. 73/54.23 |
| 2011/0009745 A1 * | 1/2011 | Seifer et al. .................. 600/437 |
| 2011/0048135 A1 * | 3/2011 | Caron ............................ 73/633 |
| 2012/0046548 A1 * | 2/2012 | Hao et al. ..................... 600/440 |

\* cited by examiner

APPARATUS AND METHOD FOR VISUALIZATION OF PARTICLES SUSPENDED IN A FLUID AND FLUID FLOW PATTERNS USING ULTRASOUND

CROSS-REFERENCE TO RELATED APPLICATIONS

The present application claims the benefit of U.S. Provisional Patent Application No. 61/379,888 for "Method And Apparatus For Visualization Of Particles And Flow Patterns Using Ultrasound" which was filed on Sep. 3, 2010, the entire contents of which is hereby specifically incorporated by reference herein for all that it discloses and teaches.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to detecting particles in fluids and, more particularly, to an apparatus and method for measuring the size, concentration and size distribution of particles in fluids, and for determining fluid flow patterns.

BACKGROUND OF THE INVENTION

It is often desirable to detect particles in fluids and determine their size distribution. Microscopes and cameras may be used to accomplish these measurements if the liquid is transparent, and the liquid can be viewed by the measurement devices. Light scattering may also be used to detect particles, but liquid transparency to the light is still a requirement. Various optical methods that use coherent light (lasers, for example) as well as incoherent light in the optical region of the electromagnetic spectrum have been reported to be useful for particle measurements in transparent or translucent fluids and in situations where particle concentrations are low to moderate. In situations where detection of the presence of particulate matter in a liquid flowing through a transparent or opaque pipe where the liquid is optically opaque, such as crude oil, conventional techniques do not work.

Additionally, it is of interest to monitor fluid flow and fluid flow patterns. This may also be achieved by visual observation, but again the liquid being studied must be optically transparent.

Ultrasonic imaging is used extensively in nondestructive testing for detecting cracks and other defects. It is also used for medical imaging to visualize various internal organs in humans or animals.

SUMMARY OF THE INVENTION

Embodiments of the present invention overcome the disadvantages and limitations of the prior art by providing an apparatus and method for monitoring liquid flow patterns and characteristics of particles in a liquid.

Another object of embodiments of the present invention is to provide an apparatus and method for noninvasively monitoring liquid flow patterns and characteristics of particles in a liquid.

Yet another object of embodiments of the invention is to provide an apparatus and method for noninvasively monitoring liquid flow patterns and characteristics of particles in an optically opaque liquid.

Still another object of embodiments of the invention is to provide an apparatus and method for noninvasive particulate detection and visualization that can be attached at any location on an oil/gas production pipe, and can be easily moved to another location as becomes necessary.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein the method for detecting particles suspended in a static or flowing fluid, hereof, includes the steps of: directing a narrow beam of pulsed ultrasonic energy from a transducer through a coupler filled with a second fluid for transmitting the ultrasonic energy into the first fluid; sweeping the transducer over a chosen angle at a selected rate such that the beam of ultrasonic energy is moved through the first fluid through the chosen angle at the selected rate; and detecting the pulse-echo return signal from the first fluid during the sweep of the transducer; whereby, particles present in the first fluid are detected.

In another aspect of the present invention and in accordance with its objects and purposes, the apparatus for detecting particles suspended in a first static or flowing fluid in a pipe or container, hereof, includes: a transducer for generating a narrow beam of pulsed ultrasonic energy directed into the first fluid, and for detecting pulse-echo return signals from the first fluid; a wobbler for sweeping the first transducer over a chosen angle at a selected rate such that the beam of ultrasonic energy is moved through the first fluid through the chosen angle at the selected rate; a dome enclosing the transducer and the wobbler; and a coupler filled with a second fluid for ultrasonically coupling the ultrasonic energy through a wall of the pipe or other container into the first fluid and out of the first fluid.

In yet another aspect of the present invention and in accordance with its objects and purposes, the method for detecting particles suspended in a first static or flowing fluid, hereof, includes the steps of: directing a narrow beam of pulsed ultrasonic energy from a first transducer into the fluid; sweeping the first transducer over a chosen angle at a selected rate such that the beam of ultrasonic energy is moved through the fluid through the chosen angle at the selected rate; and detecting pulse-echo return signals from the first fluid during the sweep of the first transducer; whereby, the particles are detected.

Benefits and advantages of embodiments of the present invention include, but are not limited to, providing an apparatus and method for noninvasively detecting and identifying particles suspended in static or flowing fluids, and for measuring fluid flow patterns, which are applicable to opaque fluids, such as crude oil and drilling mud, as examples, in pipes or tubes. Commercially available ultrasonic scanning and imaging apparatus may be used to image microscopic particles and liquid flow in real-time through solid walls. This feature makes use of the present apparatus for down hole applications possible since the scanning head may be enclosed inside of a rugged metal container or pipe.

The apparatus may be used to image small particles and fluid flow (vortices and disturbances, as examples) in optically opaque fluids, which are not otherwise possible using conventional techniques.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of a perspective view of an embodiment of the apparatus of the present invention, illustrating the ultrasound scanner electronics, the scanner head, and a pipe or tube filled with flowing liquid and particles, the scanner head being in direct connection with the liquid, while

FIGS. 3A and 3B illustrate sequential ultrasonic images over a period of several seconds showing the pattern of movement of two different sizes of particles through a stationary liquid under the influence of gravity, and the separation thereof as they fall, while

DETAILED DESCRIPTION OF THE INVENTION

Figure 1A:
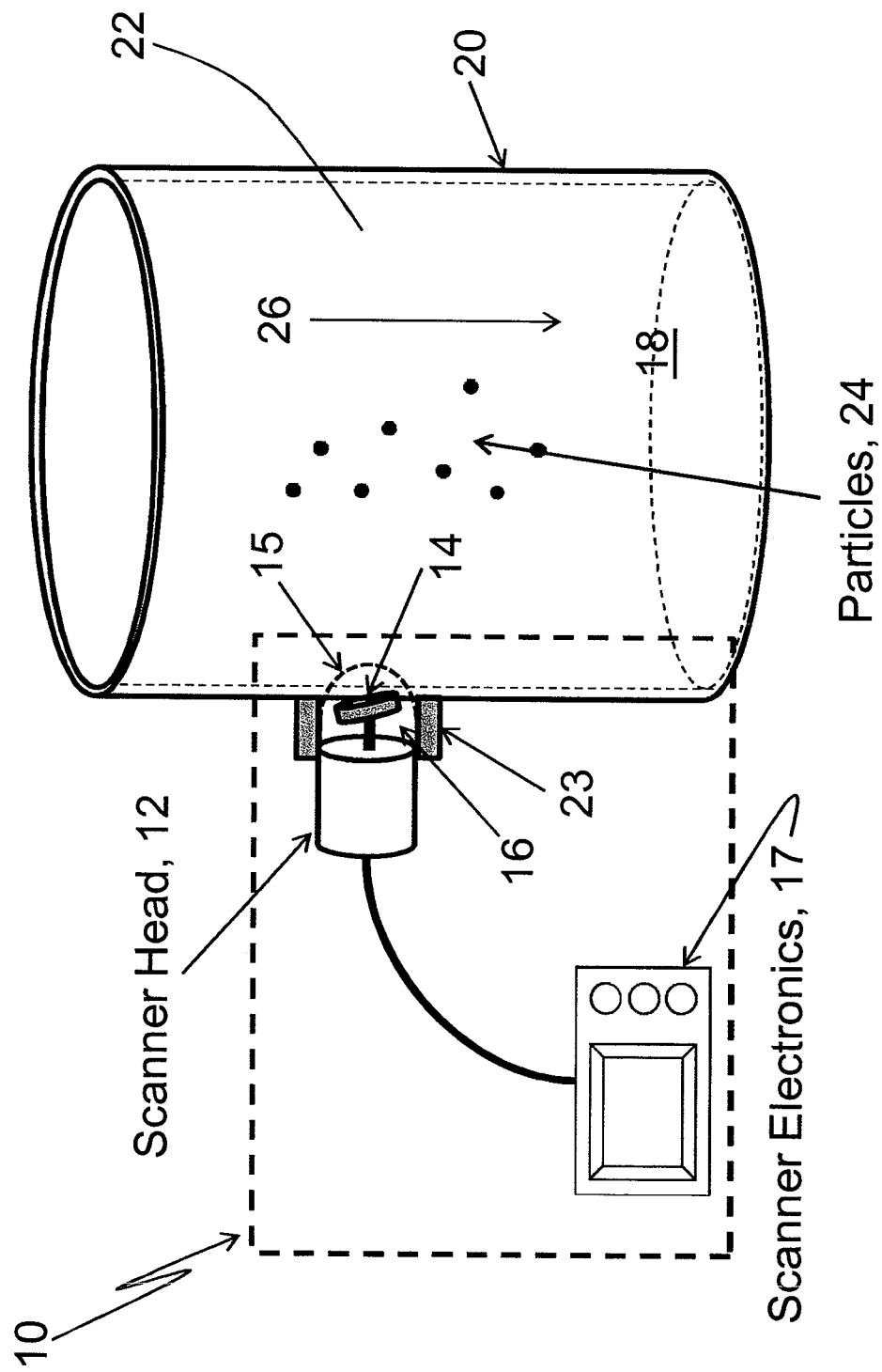

Briefly, embodiments of the present invention include an apparatus and method for noninvasively detecting and visualizing the presence of particulate matter suspended in a static or flowing fluid, and fluid flow patterns in a pipe, tube, conduit, or other container. Ultrasonic scanning and scattering of sound from particles in a fluid create a real-time image of the particles or flow patterns in liquids. Images were taken at a standard video rate of 30 frames per second, and the particles were tracked as a function of time using commercial video tracking software. The frame rate depends on the depth within the liquid to be probed, longer pathlengths requiring slower frame rates. The invention allows nanometer size particles to be imaged, including strands of DNA.

The scanner used includes a mechanical wobbler (also known as a mechanical sector scanner) that directs a sound beam generated in a piezoelectric disc transducer (1.5 cm in diameter, as an example) over a chosen angle (approximately 120°, as an example) in an oscillatory manner. The front surface of the transducer may be slightly concave to provide beam focusing, if necessary. The width of the generated sound beam (3 dB) from the transducer in water is approximately 20°. Consequently, the sound beam covers a region about 20° wide in a 120° arc perpendicular to the axis of rotation of the transducer. The transducer may have a center frequency of about 3.5 MHz, with higher or lower frequencies obtainable using appropriate transducers (for highly attenuating and optically opaque fluids, lower ultrasonic frequencies may be effectively used), and is operated in a pulse-echo mode, wherein the same transducer detects the return signal from the target region through which particles are passing and/or a flow is present. The pulse-echo measurements are made rapidly and continuously during a single sweep of the transducer over the chosen angle. The received signals are processed in the ultrasound scanner electronics module and displayed as an image in real-time.

A phased-array of ultrasound scanners may also be used for this purpose. In a phased-array system, a linear array of transducer elements, for example, 64 or 128 elements, is employed. By applying a voltage pulse to each transducer element with a small, fixed, time delay between each adjacent element, the sound beam produced by the array may be steered in an angular manner from side to side. The delay determines the angle of steering. A single receiver or multiple receivers may be used to detect the return signal. This permits electronic steering of the sound beam in place of mechanically moving a single transducer.

The scanner head includes the piezoelectric disc transducer along with a gear or other mechanical system to permit oscillatory motion inside a cylindrical compartment having a dome-shaped plastic cover which transmits sound filled with a low-viscosity fluid for permitting sound transmission and facile movement of the transducer. The dome-shaped cover also assists in the acoustic lensing of the beam, and may either be placed in contact with the liquid or coupled to the outside wall of a container or pipe. For example, good visualization was observed through a steel wall as thick as 1-cm, although more typical measurements were made through much thinner walls, approximately 2 mm thick, as an example.

Fluid flow speed can be determined by tracking the trajectory of the imaged particles that behave as tracer particles in the fluid. Terminal velocity of spherical particles in a fluid may be determined using the Stokes equation: $V_t = gd^2(\rho_s - \rho)/18\mu$, where g is the gravitational acceleration, d is the diameter of a particle, $\mu$ is the liquid viscosity, $\rho$ is the density of the liquid, and $\rho_s$ is the density of the solid particle, respectively. This velocity is orders of magnitude lower than the liquid flow speed, especially in oil, and thus the particles flow with the liquid. Further, the Stokes equation shows that if particles are dropped in a static fluid and the particle size is known, then the liquid viscosity can be determined from the terminal velocity of the particles. Conversely, if the host fluid viscosity and physical properties are known, the particle size can be determined.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1A, scanner, 10, includes scanner head, 12, which includes a mechanical wobbler for sweeping disk transducer, 14, in a plane such that the ultrasound beam generated can be scanned over a chosen angle at a selected rate. Transducer 14 is electrically excited using a train of pulses, and a sound beam is generated and transmitted. Returning signals are also detected by transducer 14. Transducer 14 may be slightly concave to improve the focusing of the sound beam, and is sealed inside of hard plastic dome, 15, which is filled with coupling fluid or gel, 16, and also assists in the focusing of the sound beam. Dome 15 also behaves as a converging lens for the return signal. A commercial ultrasound scanner designed for veterinary use was adapted for particle imaging in accordance with the teachings of the present invention, although any appropriate scanner may be used for particle imaging. As stated hereinabove, a phase array of transducer elements may effectively be used in place of the wobbler and transducer 14, there being no moving parts. The phased array would be disposed in scanner head 12 which is electrically connected to scanner electronics, 17, and converts the pulse-echo distance ranging signal received from transducer 14 into an image, and drives wobbler. The detected signal is in the form of distance from transducer 14 determined from the time-of-flight of the transmitted signal to a target and its return following reflection from the target. Scanning head 12 communicates with fluid, 18, in pipe, tube, conduit or other fluid container, 20, through a hole in wall, 22, thereof, such that plastic dome 15 containing transducer 14 is in direct contact with fluid, 18 inside pipe 20. Scanner head support, 23, affixes the head to the pipe, and includes a rubber washer for sealing scanner head dome 15 around the hole, thereby preventing fluid leakage. Fluid 18 may have particles, 24, suspended therein, and may be flowing, shown as downward direction, 26.

Figure 1B:
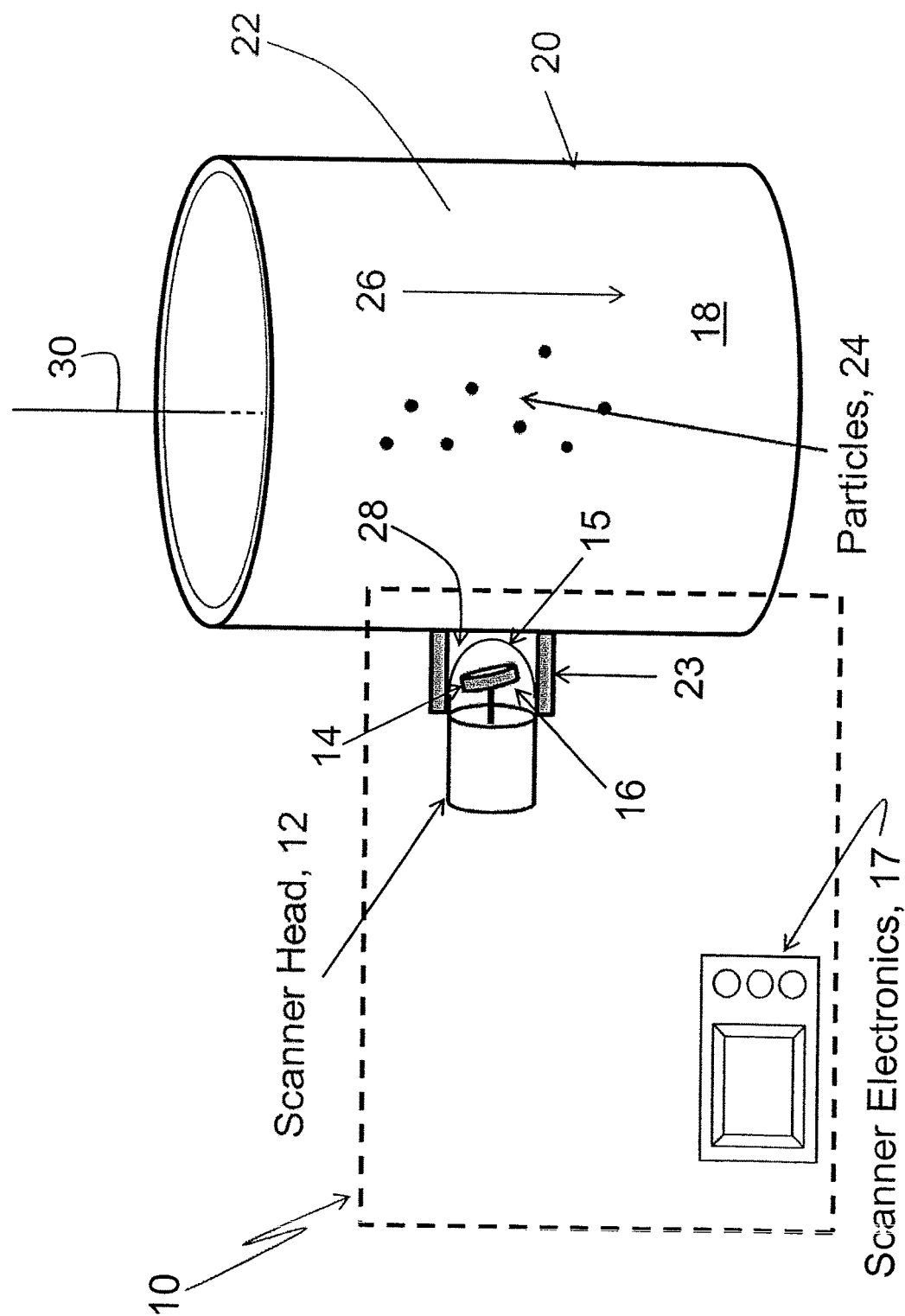
FIG. 1B is a schematic representation of another embodiment of the apparatus of the present invention illustrating the coupling of the scanner head to the exterior of the pipe using a coupling gel or other fluid without penetrating the pipe wall.

In applications where direct contact of scanner head 12 with fluid 18 is not desirable or possible, dome 15 is coupled to container wall 22 of container 20 using support 23 which also serves as reservoir, 28, filled with an ultrasonic vibration transmitting couplant material such as water or a gel, as examples, as shown in FIG. 1B. The sound beam from scanner head 12 enters fluid 18 from a generally orthogonal direction with respect to axis, 30, of container 18; in the horizontal direction for pipe 18 shown to be oriented vertically in FIG. 1B. Particles 24 of different types and sizes are dropped into the liquid from the top of container 20, which causes the particle motion to be vertical. The wall thickness of pipe 18 may be as large as 1-cm without significant degradation of the image.

Figure 1C:
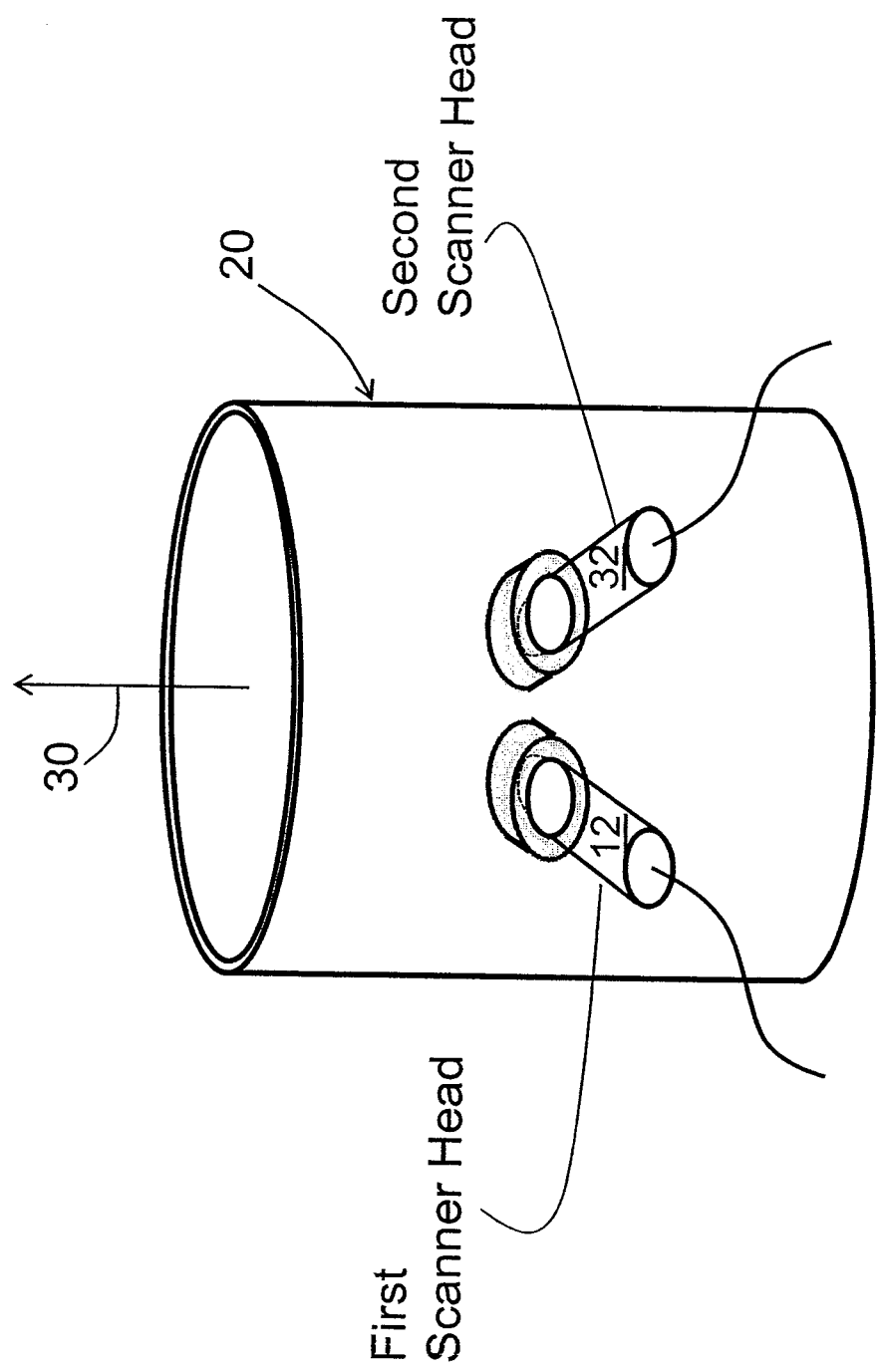
FIG. 1C shows a schematic representation of a perspective view of a two-scanner apparatus for stereoscopic three-dimensional particle of flow visualization.

The images obtained using a single scanning head illustrates a horizontal slice of the objects in that plane based on the manner in which the scanner head is disposed. Depth information in terms of time for signal return is provided. However, a stereoscopic, 3-dimensional image may be generated for obtaining particle flows and trajectories, if two identical scanning heads are electronically synchronized. As shown in FIG. 1C, scanning heads 12 and, 32, are positioned near to one another at a distance which depends on the size of pipe 20. In the case of a rectangular-shaped container, the scanner heads may be positioned orthogonal to each other. The pulses used for this measurement are tone bursts, several cycles, for example, 5 cycles, of a sine wave signal. The two transducers in heads 12 and 32 are operated at slightly different frequencies, and the received signals from each scanner head are band-pass filtered, not shown in FIG. 1C, for the measurement such that there is no interference of one scanner measurement with the other. The scanning electronics and the associated data-acquisition, not shown in FIG. 1C, system store each frame of the synchronized data from both scanning heads such that a stereoscopic output display may be presented. A modification of this measurement may be where one scanner head scans the field perpendicular to axis 30, while the other scanner head scans parallel to axis 30. This provides another observation of the particle trajectory and fluid flow in 3-dimensions. Another 3-dimensional measurement may be achieved using a single scanner head for scanning in a plane perpendicular to axis 30, while moving the scanner head up and down along axis 30. This enables both 2-dimensional scanning and 3-dimensional imaging, where multiple slices are assembled to create a 3-dimensional image. However, such an arrangement may become impractical for observing rapidly moving particles, where the mechanical oscillation of the scanner head cannot follow the movement of the particles. In such a situation, a 2-dimensional phased-array of electronically scanned piezoelectric transducers may be used, without the necessity of making corrections for beam refraction through the pipe or container wall, especially for wall thicknesses greater than 2 mm.

Figure 2C:
FIGS. 2A-2C illustrate sequential ultrasonic images over a period of several seconds of a small number of 100 μm diameter quartz particles moving through water in accordance with an embodiment of the present invention.
Figure 2C:
Figure 2B:
Figure 2A:
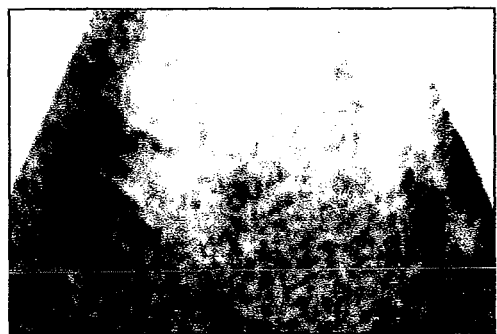

FIGS. 2A-2C show a sequence of real-time images of several 50 µm size particles dropping through a static water column and reaching terminal velocity. Individual particles can be clearly identified and tracked. The path of the detected particles appears slightly curved in the sequence of images because the ultrasound beam is scanned back and forth at a chosen angle. However, this curvature may easily be corrected. Additionally, the images of the individual particles appear blurred because of the wobbling of the transducer during the movement of the particles. This may also be corrected by applying conventional de-blurring algorithms. By tracking the location of individual particles or the center of mass of an ensemble of particles, particle velocity may be determined. If the particles are suspended in a flowing liquid, the liquid flow speed may be determined.

Figure 3C:
FIG. 3C shows the ensuing flow pattern in the liquid.
Figure 3B:
Figure 3A:

A mixture of powders having nominal sizes of about 250 µm and about 45 µm with size distributions of approximately ±5 µm were used to visualize the dynamics of the particle separation process as the particles in the mixture fall through a static column of water. FIGS. 3A-3C show a sequence of images taken over several seconds. The larger and the smaller size particles separate quickly as may be observed from FIGS. 3A and 3B. FIG. 3C shows complete separation of the two particle sizes, such that the larger particles are no longer in view. The fast movement of the larger particles produces eddies, which can be observed in FIG. 3C. If water 18 in container 20 is stirred, flow patterns and vortices may be observed in the absence of particles. Ultrasonic visualization studies were also performed in opaque liquids, such as 10W-40 motor oil and drilling mud, both with direct contact and noninvasively for macroscopic articles, such as wrenches and springs, as examples.

Figure 4C:
FIGS. 4A and 4B show a comparison of images using a visual camera with the ultrasonic scanner images of FIGS. 4C and 4D, respectively, for a small number of 5 nm size particles suspended in water.
Figure 4D:
Figure 4A:
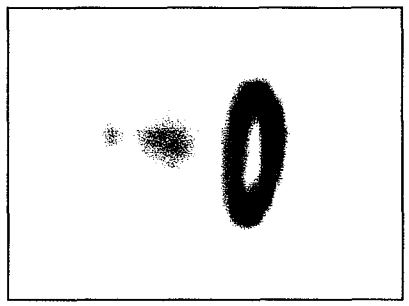
Figure 4B:
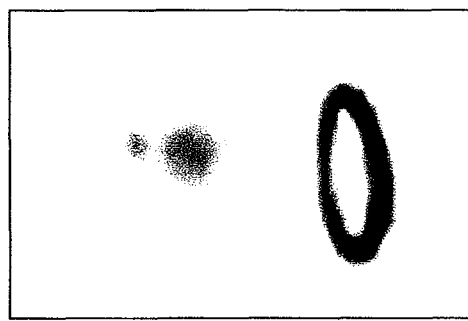

FIGS. 4A-4D show the visualization of nano-sized particles using the apparatus of the present invention. A suspension of 5-nm carbon-coated diamond particles in water was prepared, and one drop of this suspension was placed on the top surface of water-filled transparent container 20. Both visual images and ultrasonic images were made simultaneously, although the scales of the two sets of pictures are different since the visual camera and the ultrasound scanner were disposed approximately orthogonally to each other. FIGS. 4A and 4B show the visual pictures and FIGS. 4C and 4D show the corresponding ultrasound pictures. Since the ultrasound pictures are at angle, the vortex ring formed appears as two separated masses. Bovine DNA strands were also successfully imaged by the present invention, which illustrates that embodiments of the invention are effective for imaging nano-sized particles. It is contemplated that embodiments of the present invention can be used to image carbon nanotubes and other nanowires suspended in optically opaque host fluids, but this may require significantly higher frequencies, such as 50 MHz for which the sound wavelength in water is 30 µm. Individual carbon nanotubes may be difficult to resolve, but small clusters of such particles are likely to be observable since 5 nm diamond particles have been observed in accordance with the teachings of embodiments of the present invention.

All liquid flow studies in optically transparent liquids presently use color dyes to accentuate the flow patterns for visual observations. However, flow patterns in crude oil or other optically opaque fluids cannot be studied using such methods. The present invention enables such measurements to be made.

Many refinements of the embodiments of the present apparatus are possible. For example, better quality images can be made using higher frequency scanners; that is, for small distances, frequencies up to 50 MHz may be used to obtain high resolution images. Commercial scanners determine the transit time from the pulse-echo measurement, and generate images showing the location of particles as a function of distance from the transducer. If two scanners are synchronized and placed at different locations at an angle to each other, stereoscopic, 3-dimensional imaging can be obtained. Return echo signal can also be analyzed by frequency conversion, and frequency dependent attenuation can be used for image correction purposes.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for visualizing particles suspended in a first static or flowing fluid in a container having an axis, comprising:
    directing a beam of pulsed ultrasonic energy from a first transducer through a coupler containing a second fluid for transmitting the ultrasonic energy into the first fluid;
    sweeping the first transducer over a chosen angle relative to the axis at a selected rate such that the beam of ultrasonic energy is moved through the first fluid through the chosen angle at the selected rate; and
    detecting pulse-echo return signals reflected from the particles in the first fluid during the sweep of the transducer;
    whereby, the particles are visualized.

2. The method of claim 1, wherein said step of detecting pulse-echo return signals is achieved using the first transducer.

3. The method of claim 1, wherein the first transducer is concave.

4. The method of claim 1, wherein said steps of directing a beam of pulsed ultrasonic energy from a transducer into the fluid, and detecting the pulse-echo return signal reflected from the particles are performed noninvasively.

5. The method of claim 1, further comprising the step of sweeping the first transducer in a plane in an oscillatory manner.

6. The method of claim 1, further comprising the steps of processing the return signal using ultrasound scanner electronics, whereby an image of said particles is generated in real time; and displaying the real-time image such that said particles are visualized.

7. The method of claim 6, wherein said step of processing the return signal comprises detecting flow patterns in said first fluid.

8. The method of claim 1, further comprising the steps of tracking the motion of the particles in time; and determining the flow speed of said first fluid.

9. The method of claim 1, further comprising the steps of measuring the terminal velocity of said particles; and determining the viscosity of said first fluid.

10. The method of claim 1, further comprising the step of determining the size of the particles.

11. The method of claim 1, further comprising:
    directing a second beam of pulsed ultrasonic energy from a second transducer at a selected fixed angle from the first beam of ultrasonic energy through a coupler filled with a third fluid for transmitting the ultrasonic energy into said first fluid;
    sweeping the second transducer over a second chosen angle at a second selected rate such that the second beam of ultrasonic energy is moved through said first fluid through the second chosen angle at the second selected rate; and
    detecting second pulse-echo return signals reflected from the particles in the first fluid during the sweep of the second transducer;
    whereby stereoscopic imaging of said particles is obtained, thereby permitting 3-dimensional visualization.

12. An apparatus for visualizing particles suspended in a first static or flowing fluid in a pipe or container having an axis, comprising:
    a first transducer for generating a beam of pulsed ultrasonic energy directed into said first fluid, and for detecting pulse-echo return signals reflected from the particles in said first fluid;
    a first wobblier for sweeping said first transducer over a chosen angle relative to the axis at a selected rate such that the beam of ultrasonic energy is moved through said first fluid through the chosen angle at the selected rate;
    a first dome enclosing said transducer and said wobbler; and
    a first coupler filled with a second fluid for ultrasonically coupling the ultrasonic energy through a wall of said pipe or other container into said first fluid and out of said first fluid.

13. The apparatus of claim 12, wherein said first transducer is concave.

14. The apparatus of claim 12, wherein said second fluid is chosen from water and gels.

15. The apparatus of claim 12, wherein said dome is filled with an ultrasound transmitting fluid.

16. The apparatus of claim 12, wherein said wobbler sweeps the transducer in a planar oscillatory manner.

17. The apparatus of claim 12, further comprising ultrasound scanner electronics for generating an image in real time; and a display for visualizing the real-time image, such that said particles are observable.

18. The apparatus of claim 17, wherein said ultrasound scanner electronics and said display visualize flow patterns in the first fluid.

19. The apparatus of claim 17, further comprising:
    a second transducer for generating a beam of pulsed ultrasonic energy, and for detecting pulse-echo return signals reflected from the particles in said first fluid, said second transducer being disposed at a chosen angle to said first transducer;

a second wobbler for sweeping said second transducer over a chosen angle at a selected rate such that the beam of ultrasonic energy is moved through said first fluid through the chosen angle at the selected rate;

a second dome enclosing said second transducer and said second wobbler; and a second coupler filled with a third fluid for ultrasonically coupling the ultrasonic energy through a wall of said pipe or other container into said first fluid.

20. A method for visualizing particles suspended in a first static or flowing fluid in a container having an axis, comprising:

directing a beam of pulsed ultrasonic energy from a first transducer into said fluid;

sweeping the first transducer over a chosen angle relative to the axis at a selected rate such that the beam of ultrasonic energy is moved through the fluid through the chosen angle at the selected rate; and detecting pulse-echo return signals reflected from the particles in the first fluid during the sweep of the first transducer;

whereby, the particles are visualized.

21. The method of claim 20, wherein said step of detecting pulse-echo return signals is achieved using the first transducer.

22. The method of claim 20, wherein the first transducer is concave.

23. The method of claim 20, wherein said steps of directing a beam of pulsed ultrasonic energy from a transducer into the fluid, and detecting the pulse-echo return signal reflected from the particles are performed through a hole in the container.

24. The method of claim 20, further comprising the step of sweeping the first transducer in a planar oscillatory manner.

25. The method of claim 20, further comprising the steps of processing the return signal using ultrasound scanner electronics, whereby an image is generated in real time; and displaying the real-time image such that the particles are visualized.

26. The method of claim 25, wherein said step of processing the return signal comprises detecting flow patterns in the fluid.

27. The method of claim 20, further comprising the steps of tracking the motion of the particles in time; and determining the flow speed of the fluid.

28. The method of claim 20, further comprising the steps of measuring the terminal velocity of the particles; and determining the viscosity of the fluid.

29. The method of claim 20, further comprising the step of determining the size of the particles.

30. The method of claim 20, further comprising:

directing a second beam of pulsed ultrasonic energy from a second transducer at a selected fixed angle from the first beam of ultrasonic energy into the fluid;

sweeping the second transducer over a second chosen angle at a second selected rate such that the second beam of ultrasonic energy is moved through the first fluid through the second chosen angle at the second selected rate; and detecting second pulse-echo return signals reflected from the particles in the fluid during the sweep of the second transducer;

whereby stereoscopic imaging of the particles is obtained, thereby permitting 3-dimensional visualization.

* * * * *

UNITED STATES PATENT AND TRADEMARK OFFICE
CERTIFICATE OF CORRECTION

PATENT NO. : 10,605,640 B2  
APPLICATION NO. : 13/225787  
DATED : March 31, 2020  
INVENTOR(S) : Sinha et al.

Page 1 of 1

It is certified that error appears in the above-identified patent and that said Letters Patent is hereby corrected as shown below:

In the Claims

<u>Column 8</u>
Line 36, "wobblier" should read --wobbler--

Signed and Sealed this
Twenty-sixth Day of May, 2020

Andrei Iancu
*Director of the United States Patent and Trademark Office*